United States Patent
Rowlen et al.

(10) Patent No.: US 9,360,433 B1
(45) Date of Patent: Jun. 7, 2016

(54) DETECTION OF AGGLUTINATION BY OPTICAL DENSITY MEASUREMENT

(71) Applicant: InDevR, Inc., Boulder, CO (US)

(72) Inventors: Kathy Lou Rowlen, Boulder, CO (US); Jean-Luc Fraikin, Boulder, CO (US); John William Birks, Boulder, CO (US); Craig J. Williford, Boulder, CO (US)

(73) Assignee: InDevR, Inc., Boulder, CO (US)

( * ) Notice: Subject to any disclaimer, the term of this patent is extended or adjusted under 35 U.S.C. 154(b) by 0 days.

(21) Appl. No.: 14/279,821

(22) Filed: May 16, 2014

Related U.S. Application Data

(60) Provisional application No. 61/825,947, filed on May 21, 2013.

(51) Int. Cl.
| | |
|---|---|
| *G01N 21/82* | (2006.01) |
| *G01N 33/53* | (2006.01) |
| *G01N 33/80* | (2006.01) |
| *G01N 33/569* | (2006.01) |

(52) U.S. Cl.
CPC .......... *G01N 21/82* (2013.01); *G01N 33/56983* (2013.01); *G01N 33/80* (2013.01); *G01N 2021/825* (2013.01)

(58) Field of Classification Search
None
See application file for complete search history.

(56) References Cited

U.S. PATENT DOCUMENTS

| | | | |
|---|---|---|---|
| 3,819,271 A | 6/1974 | Gerisch | |
| 4,452,759 A | 6/1984 | Takekawa | |
| 4,575,492 A | 3/1986 | David | |
| 4,597,944 A | 7/1986 | Cottingham | |
| 4,760,030 A | 7/1988 | Peterson | |
| 4,829,011 A | 5/1989 | Gibbons | |
| 5,043,289 A | 8/1991 | Serres | |
| 5,169,601 A | 12/1992 | Ohta | |
| 5,283,178 A * | 2/1994 | Kessler et al. | 435/7.25 |
| 5,922,551 A | 7/1999 | Durbin | |
| 6,051,191 A * | 4/2000 | Ireland | 422/553 |
| 2009/0325148 A1 | 12/2009 | Kachurin | |
| 2012/3016079 | 12/2012 | Rowlen | |

FOREIGN PATENT DOCUMENTS

| | | | | |
|---|---|---|---|---|
| DE | 2915145 | * | 4/1979 | G01N 33/16 |
| EP | 0198327 | | 10/1986 | |
| EP | 0588969 | | 3/1994 | |
| WO | WO 92/22880 | | 12/1998 | |
| WO | WO 2012/174014 | | 12/2012 | |

OTHER PUBLICATIONS

Aubert et al (Journal of Immunological Methods 186:323-328, 1995.*

* cited by examiner

*Primary Examiner* — Stacy B Chen
(74) *Attorney, Agent, or Firm* — Lathrop & Gage LLP

(57) ABSTRACT

A system for the indirect detection of agglutination in an agglutination assay using optical density measurement and a reaction vessel. Light emitted by light source is transmitted through reaction vessel containing components of an agglutination reaction that is detected by light detector. As particles in the reaction vessel settle in the absence of agglutination they are concentrated in a reaction vessel lower volume and increase the optical density of the light path through the reaction vessel. Light detector generates an output signal related to said optical density. Said output signal is read and interpreted by an instrument to detect a presence or absence of agglutination. Other embodiments are described and shown.

12 Claims, 9 Drawing Sheets

SECTION A-A

DETECTION OF AGGLUTINATION BY OPTICAL DENSITY MEASUREMENT

RELATED APPLICATIONS

This application claims priority to U.S. Provisional Application No. 61/825,947, filed May 21, 2013, the entirety of which is hereby incorporated by reference.

STATEMENT REGARDING FEDERALLY SPONSORED RESEARCH AND DEVELOPMENT

This invention was made with Government support under Grant/Contract No. R43 AI102318 awarded by NIH/NIAID. The Government may have certain rights in the technology of this patent application.

BACKGROUND

An agglutination assay or agglutination reaction is an important and widely known technique in the biological and chemical sciences for detecting and/or quantifying chemical reagents. Agglutination assays have been used in a wide variety of applications to detect biological or chemical entities. For example, agglutination assays have been used to detect bacteria such as *Mycobacteria leprae* (leprosy) and tuberculosis, *Vibrio cholera* (cholera), *Yersinia enterolytica*, *Borrelia burgdorferi* (Lyme disease), and other bacteria. Agglutination tests have also been used to detect viral pathogens including HIV, Herpes simplex, cytomegalovirus, influenza and other viruses. Agglutination assays have also been used to determine blood type, and to detect antibodies or antigens in a variety of biological fluids such as saliva, urine, blood or serum. Applications of various embodiments of detection of agglutination by optical density measurement discussed in this application include detection of agglutination in any agglutination assay, without limitation or modification to any specific goals of the agglutination assay itself, such as to detect a particular virus or other entity.

In a type of agglutination assay, particles are suspended in a reaction medium and one or more reagents are added. The particles may be synthetic or naturally occurring, for example, cells. In the presence of a sufficient quantity of a specific agglutination agent, under conditions suitable for agglutination, the agglutination agent will cause clumping of the particles and one or more complexes of particles will form. These clumps may be of such a structure than they prevent particles from settling under the influence of gravity. For example, if the container in which the agglutination reaction is contained has a constrictions, such as, a throat or smaller diameter section, the clumping of particles into one or more complexes inhibits the clumped particles from settling through the constriction whereas if agglutination does not occur, the particles move through the constriction to settle at a bottom of the container. Throughout this application, the process of forming of one or more complexes that prevent or inhibit settling of particles under the influence of gravity or other force will be referred to as agglutination.

An agglutination assay has long been used as a method for detecting the presence of biological agents in a sample. As a specific example, in a hemagglutination (HA) assay, erythrocytes can be used as the particles and the agglutinating agent can be influenza virus particles. In such an HA assay, the influenza particles, each having multiple receptors with the ability to bind to erythrocytes, serve as cross-linking agents and generate cross-linkages between erythrocytes. If the concentration of viruses in a sample is sufficiently high, under conditions suitable for agglutination, the erythrocytes will agglutinate.

The HA assay is commonly used as a semi-quantitative method to determine the concentration of virus (titer) in an unknown sample. To measure the titer of a virus in a sample, serial dilutions of the sample are prepared and combined with a standard concentration of erythrocytes in a reservoir under conditions that are suitable to allow agglutination to occur. At sufficiently high concentrations of virus relative to the concentration of erythrocytes, the virus will cause agglutination of erythrocytes, while at sufficiently low concentrations of the virus agglutination will not occur. By determining the highest dilution at which agglutination occurs for a known concentration of erythrocytes, an estimate of the concentration of the virus can be obtained.

A variation of the HA assay is the hemagglutination inhibition (HAI) assay. The HAI assay is widely used as a semi-quantitative method for determining the concentration of specific influenza antibodies in an unknown sample. As an example, the unknown sample in the HAI assay may be a blood serum sample from a human subject that has been vaccinated by exposure to a specific type of influenza hemagglutinin, and the concentration of antibodies to the specific type of influenza hemagglutinin in the serum sample may indicate the efficacy of the vaccine in generating immunity to the specific type of influenza virus. In the HAI assay, serial dilutions of the unknown sample are prepared and mixed with a fixed concentration of erythrocytes and virus particles. At sufficiently high antibody concentrations, antibodies with binding affinity for the specific virus will bind to the virus particles and block their ability to cross-link erythrocytes, thus preventing agglutination. At sufficiently low antibody concentrations (or in the absence of antibodies with binding affinity to the specific virus) the virus will cause agglutination of erythrocytes to occur. The highest dilution factor of the unknown sample that prevents agglutination is the HAI titer value, and serves as a metric representing the concentration of the antibodies with binding affinity for the specific virus in the unknown sample.

The HA and the HAI assays are widely used in the influenza vaccine industry to estimate the concentration of both viruses and virus-specific antibodies in unknown samples. Typically, the assay is used to analyze multiple unknown samples in parallel in a 96-well plate format, together with a standard (known) sample for calibration and a set of appropriate control tests. To improve the accuracy of the resulting measurements, serially-diluted samples are often tested in duplicate or triplicate at each concentration. Thus, for each unknown sample a large number of wells must be evaluated for the presence or absence of agglutination.

Detection of agglutination of erythrocytes or other particles in a reaction reservoir in an agglutination assay is typically accomplished by examining the bottom of the reaction vessel after a period of time sufficient to allow free particles to settle to the bottom. The assay is typically performed in a cylindrical reservoir with a round or conical bottom shape forming a constriction or throat. In the absence of agglutination, particles settle on the bottom of the reservoir and form a "button," a region of high density particles. When agglutination occurs, the rigidity of the cross-linked particle complex prevents particles from settling and no button is observed on the bottom of the reservoir.

In practice, presence or absence of a button at the bottom of the reaction vessel is often determined by the unaided eye, a method that poses significant drawbacks. For example, this method requires careful assessment of each well and manual recordation of results, both of which are time consuming. Another example is that due to incomplete button formation (often referred to as a "halo effect"), the user routinely must tilt the entire plate at an angle and characterize the dynamic behavior of the incomplete button in order to interpret the data. Both of these examples of requirements in interpretation of the assay as well as others contribute to a significant level of subjectivity in interpretation of results, and variability in results between users.

The process of reading hemagglutination assay results is thus tedious, time-consuming, and requires user expertise and experience to reduce subjectivity and variability. These limitations restrict the number of personnel capable of providing reliable interpretation, and often result in plate reading being a bottleneck in the overall process of evaluating unknown samples. For a large company, central laboratory facility or organization, such as the US Centers for Disease Control and Prevention ("CDC"), that processes large numbers of unknown samples using agglutination assays, the manual analysis of agglutination assay results is a major limitation to throughput. Thus, an automated method for determining the presence or absence of agglutination is desirable.

Two main approaches have been previously described for the automated, optical detection of agglutination. In the first approach (direct approach), direct measurements of changes in the bulk optical properties of the reaction materials are made before and after cross-linking of particles to form clumps. A known or calibrated difference in an observed optical property of agglutinated and non-agglutinated reaction materials is used to detect the occurrence of agglutination. Examples of such optical properties include the tendency of the bulk reaction materials to scatter light, or the optical density of the bulk reaction materials. With this direct approach, a signal is generated in the case that agglutination occurs, and no significant signal is detected in the absence of agglutination. Examples of this approach are described in U.S. Pat. No. 4,829,011 to Biotrack, Inc. (1987), U.S. Pat. No. 4,760,030 to Syntex U.S.A., Inc. (1984), U.S. Pat. No. 3,819,271 to Max-Planck Gesellschaft Zur Forderung der Wissenschaften e.V. (1974), U.S. Pat. No. 4,597,944 to Cottingham (1986), U.S. Pat. No. 5,043,289 to Serres (1991), and U.S. Pat. No. 5,922,551 to Accumetrics, Inc. (1999).

Agglutination detection methods that employ the direct approach suffer from various drawbacks. For example, components of the agglutination reaction may absorb light in a wavelength-dependent manner, limiting the wavelengths of light that can be used to measure the optical properties of the reaction or limiting the media in which the agglutination experiment can be performed. As another example, non-specific agglutination of a small fraction of the particles in the reaction may cause significant changes in the bulk optical property being measured, leading to results that are false or difficult to interpret. As another example, in a scattering measurement the size of particles affects their scattering cross-section, thus limiting the size of particles or the wavelength of light that can be used in the assay. As another example, light absorption of some particles such as erythrocytes varies with oxygenation, causing changes in optical properties of the reaction in the absence of agglutination that may be misinterpreted as agglutination. Thus, while a few examples are provided, there are limitations to the utility of direct methods of optical detection of agglutination.

The second approach to optical detection of agglutination is indirect. After sufficient time for particles to have settled to the bottom of a reaction vessel, an image of the bottom of the vessel is formed, recorded and analyzed. In this method, a signal is generated in the absence of agglutination: particles that have settled in the absence of agglutination generate a pattern on the bottom of the reaction vessel that is detectable by analyzing the image of the bottom of the vessel.

Several examples of automated detection of agglutination by such indirect methods have been previously described, for example, in European patent application EP0588969A1 to Abbott Laboratories (1991), patent EP0198327 to Green Cross Corporation (1985), and U.S. Pat. No. 5,169,601 to Suzuki Motor Corp. (1990), U.S. Pat. No. 4,452,759 to Olympus Optical Company Ltd. (1980), U.S. Pat. No. 4,575,492 to Commissariat a l'Energie Atomique (1986), and U.S. Patent Application US2009/0325148 to Vaxdesign, Inc. (2008). While these methods describe various automated approaches to indirect detection of agglutination, they share a common element that the bottom of the reaction vessel is spatially imaged in at least one dimension to map the distribution of settled particles.

One disadvantage of these indirect optical methods is the requirement of considerable hardware such as focusing optics to create an image on an image plane or surface. Another disadvantage of these indirect optical methods is the requirement of either an array of light sensors for each well or a single sensor combined with mechanical hardware for scanning the single sensor across the bottom of each well to collect the image formed. This specialized imaging and image-collecting hardware adds to the cost and complexity of an instrument, and in the case of a scanning imaging system, increases the time required to evaluate agglutination in each well.

Another disadvantage associated with indirect measurement of the imaging type is that it is difficult to collect substantially continual measurements of the agglutination process with these methods. The time required to scan a sensor across the bottom of a well to form an image limits the time resolution of substantially continual measurements, thus limiting the potential utility of such measurements in detecting rapid changes during agglutination. The fixed sensor array method for collecting an image of the bottom of the reaction vessel to detect agglutination is limited by the time required to process the image at each time point, which either limits the time resolution of the data collection or requires a large amount of time after the assay is complete to process each image from the time series.

Another disadvantage associated with indirect measurement is that it requires imaging is that the approach is not easily amenable to making parallel measurements of multiple wells. The cost and complexity of the imaging optics and sensor array, as well as the difficulty of properly aligning such optics for each well prohibits large-array scaling of such methods.

The drawbacks of the conventional direct and indirect measuring methods makes improved optical detection methods desirous. The need for improvement is demonstrated in part as after nearly thirty years since the development of the above optical methods of agglutination detection: a single CDC laboratory will, for sustained periods, evaluate thousands of reaction vessels each day for agglutination in HA or HAI assays, and to do so they evaluate the samples using the unaided eye of highly experienced, trained scientists rather than one of the aforementioned detection methods. Against this background, the technology of the present application provides an automated method of detecting agglutination in an agglutination reaction.

SUMMARY

In accordance with one aspect of the technology of the present application, an instrument and method comprise an automated indirect determination of agglutination by measurement of optical density.

This Summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

Accordingly, several advantages of one or more aspects of the technology over conventional optical detection include, but are not limited to, the following: to provide an automated method for detecting agglutination of particles in an agglutination assay that reduces subjectivity and variability in interpretation, to reduce the user expertise and experience required for interpretation, to reduce the need to create an image of the bottom of a well, to perform the detection more rapidly than scanning an image of the bottom of a well, to reduce or eliminate the requirement of optical components for generating an image of the bottom of a well, to reduce the need for optical elements, to allow parallel measurements of multiple wells, such as in a 96-well plate format, and to permit regular measurements during the agglutination process. The technology of the present application in one or more aspects provides a reaction vessel to facilitate detection of agglutination by optical density. Other advantages of one or more aspects will be apparent from a consideration of the drawings and ensuing description.

BRIEF DESCRIPTION OF THE DRAWINGS

Non-limiting and non-exhaustive embodiment of the technology of the present application, including the preferred embodiment, are described with reference to the following figures, herein like reference numerals refer to like parts throughout the various views unless otherwise specified.

Drawings-Reference Numerals

Figure 1:
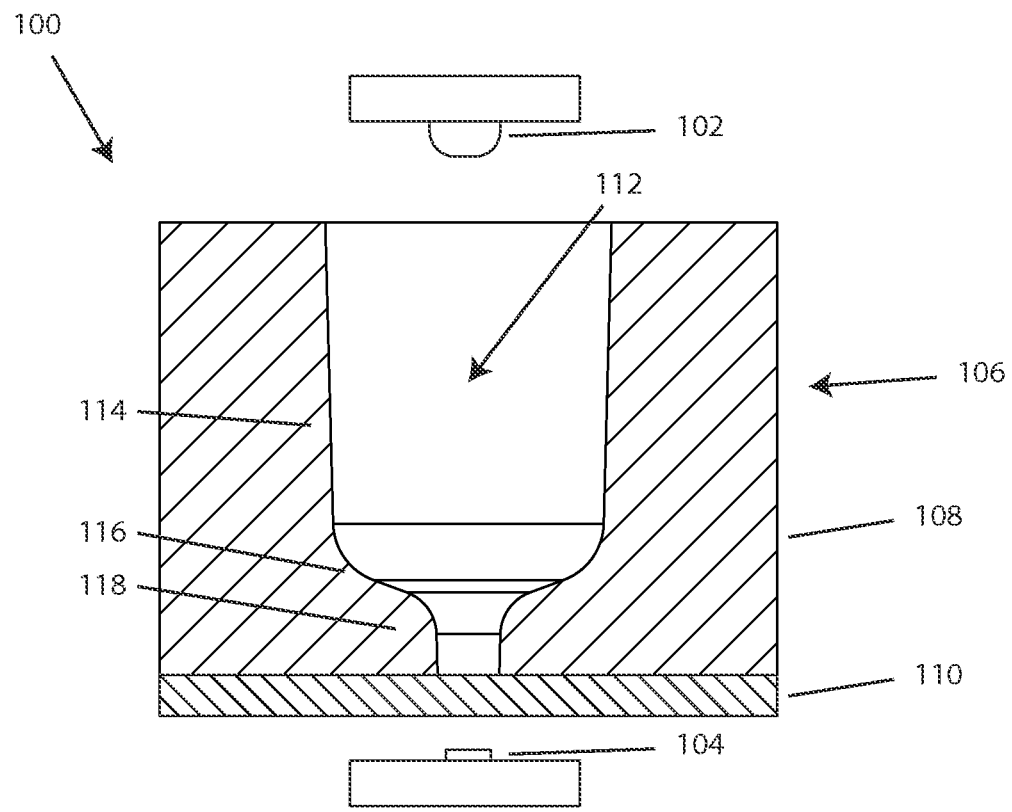
FIG. 1 shows a schematic illustration of an optical density agglutination detection system in accordance with the technology of the present application.

| | |
|---|---|
| 100 Agglutination detection system | 300 Well plate |
| 102 Light Source | 302 Well plate top |
| 104 Light Detector | 304 Well plate bottom |
| 106 Well plate | 400 Well plate |
| 108 Well plate top | 600 Well plate |
| 110 Well plate bottom | 602 Well plate top |

-continued

Drawings-Reference Numerals

| | |
|---|---|
| 112 Reaction Vessel | 604 Well plate shield |
| 114 Reaction Vessel Upper Volume | 700 Arrayed well plate |
| 116 Reaction Vessel transition region | 702 Reaction vessel |
| 118 Reaction Vessel Lower Volume | 800 Arrayed light source |
| 200 Particle | 802 Arrayed light detector |
| 202 Agglutination complex | 804 Distributed light source |
| 204 Agglutination cross-linkage | 806 Isolated arrayed light detector |

DETAILED DESCRIPTION

The technology of the present application will now be described more fully below with reference to the accompanying figures, which form a part hereof and show, by way of illustration, specific exemplary embodiments. These embodiments are disclosed in sufficient detail to enable those skilled in the art to practice the technology of the present application. However, embodiments disclosed herein may be implemented in many different forms and should not be construed as being limited to the embodiments set forth herein. The following detailed description is therefore, not to be taken in a limiting sense. Moreover, the technology of the present application will be described with relation to exemplary embodiments. The word "exemplary" is used herein to mean "serving as an example, instance, or illustration." Any embodiment described herein as exemplary is not necessarily to be construed as preferred or advantageous over other embodiments. Additionally, unless specifically identified otherwise, all embodiments described herein should be considered exemplary.

FIG. 1

First Embodiment

One embodiment of the optical density agglutination detection system 100 is illustrated in FIG. 1. The agglutination detection system 100 comprises light source 102, light detector 104 and well plate 106.

In one embodiment, light source 102 is a light emitting diode with a peak emission wavelength of 532 nm. However, light source 102 can be any type of light source including, but not limited to, a light emitting diode with a peak wavelength other than 532 nm, a laser, or an incandescent light source. The light source 102 may emit light in a narrow band of wavelengths or a broad band. Light source 102 may also be an array of light sources; for example, a pixel array. In other embodiments, light source 102 may incorporate optical components, such as reflectors or fibers, to direct emitted light towards light detector 104. On reading the disclosure, one who is skilled in the art will recognize that in other embodiments, light source 102 may be an ambient source. In some aspects, the ambient sources could be considered peripheral to the agglutination detection system 100, such light sources may include, for example, the sun or other source of ambient light.

In one embodiment, light detector 104 is an ambient light sensing photodiode available from DigiKey Corporation of Thief River Falls, Minn. However, light detector 104 can be any photosensitive detector or an array of photosensitive detectors capable of generating an electrical signal that varies with the intensity of light incident on its detector surface. The electrical signal may be a voltage or current signal.

In one embodiment, well plate 106 comprises two layers: well plate top 108 and well plate bottom 110. Surfaces of plate top 108 and plate bottom 110 form the sides and bottom of a reaction vessel 112 in which to perform one or more agglutination reactions. The plate top 108 has a top surface, but reaction vessel 112 is shown as open to the top. However, in certain aspects, the top of reaction vessel 112 may be partially or completely closed by a clear or translucent panel.

The reaction vessel 112 includes an upper volume 114 that has a relatively consistent cross sectional area along the volume and a lower volume 118 that has a relatively consistent cross sectional area along the volume. The cross sectional area of the upper volume 114 is generally greater than the cross sectional area of the lower volume. The reaction vessel 112 includes a transition region 116 between the upper volume 114 and the lower volume 118. The transition region 116 has a cross sectional area along the volume that varies from the upper volume to the lower volume. As shown the transition region 116 curved or arced. In still other embodiments, the transition region 116 may be frustoconical in shape.

In one embodiment, well plate top 108 is an opaque plastic, for example, pigmented polypropylene, so as to restrict the light detected by light detector 104 to that light which has traveled through the reaction vessel 112 and more particularly, the lower volume 118 of the reaction vessel. However, well plate top 108 can consist of many other materials with consideration taken for manufacturability, biocompatibility, and opacity. In one embodiment, well plate top 108 is manufactured by injection molding, is biocompatible with components of an agglutination reaction, and prohibits transmission of most of the wavelengths of light capable of being detected by light detector 104.

In other embodiments, appropriate opacity properties may be imparted to well plate top 108 by applying a coating with a suitable material, such as black paint. In other embodiments, appropriate biocompatibility properties may also be imparted to the part by coating with suitable materials such as bovine serum albumin (BSA) or polymer coatings.

In one embodiment, well plate bottom 110 is a transparent plastic, for example, acrylic, so as to permit light emitted from light source 102 to travel through reaction vessel 112 and reach the light detector 104. However, well plate bottom 110 can be one or a combination of many other materials with consideration taken for manufacturability, biocompatibility and transparency. In one embodiment, well plate bottom 110 is manufactured by extrusion, is biocompatible with components of an agglutination reaction and transmits most of the wavelengths of light capable of being detected by light detector 104. In certain embodiments, the well plate bottom 110 may be a combination of opaque and transparent material where the well plate bottom 110 is only transparent proximate the lower volume 118 and light detector 104. While not shown, alternative configurations of the light source 102 and light detector 104 are possible. For example, the light source 102 may be provided along a side of the reaction vessel 112 (rather than the top) and aligned generally with the lower volume. The light detector 104 may further be aligned with the light source 102 on an opposed side of the reaction vessel 112. A bore, not shown, would be provided in the plate top 108 from the light source 102 to the light detector 104 such that light travels along the bore and through the lower volume 118 of the reaction vessel 112. In one embodiment, the shape of reaction vessel 112 is such that particles settling in reaction vessel 112 are caused to concentrate about a light path between light source 102 and light detector 104 in the lower volume 118. As can be appreciated, the particles settle by force of gravity. In an alternative embodiment, other forces may cause the particles to move or concentrate about a light path. These other forces may include, for example, current generated by pumps, convection forces, anodes and cathodes, or the like.

In one embodiment, the shape of reaction vessel 112 has cylindrical symmetry comprising an upper volume 114 and a lower volume 118, lower volume 118 having smaller diameter than upper volume 114 so as to concentrate particles settling during the course of an agglutination reaction into a region with smaller cross-sectional area. Typically, the size of reaction vessel 112 may be equivalent to the size of a typical well in a 96-well plate. However, alternative sizes are possible. In an embodiment, the cross-sectional diameter of the upper volume 114 is approximately 14 mm and the cross-sectional diameter of the lower volume 118 is approximately 3 mm, and the height of reaction vessel 112 from top to bottom is about 11 mm. Typically, lower volume 118 is large enough to accommodate all of the particles in the reaction vessel 112 that do not clump as part of the agglutination, but is a small fraction of the overall volume of the reaction vessel 112 so as to increase the factor by which particles settling in an agglutination reaction are concentrated. The bottom surface of reaction vessel 112 is flat in FIG. 1. In other embodiments the bottom surface may be rounded or textured.

As shown in FIG. 1, the profile of transition region 116 between the upper volume 114 and lower volume 118 slopes downward and inward towards the light path so as to guide settling particles towards the light path along the surface of the reaction vessel and concentrate them in the lower volume 118. In FIG. 1 transition region 116 has a profile that comprises curved sections. In other embodiments the profile of transition region 116 may take other shapes, for example a frustoconical shape which includes an angular transition from large diameter to small diameter, with the provision that transition region 116 slopes generally downwards and inwards towards the light path to concentrate settling particles in lower volume 118.

Figure 2C:
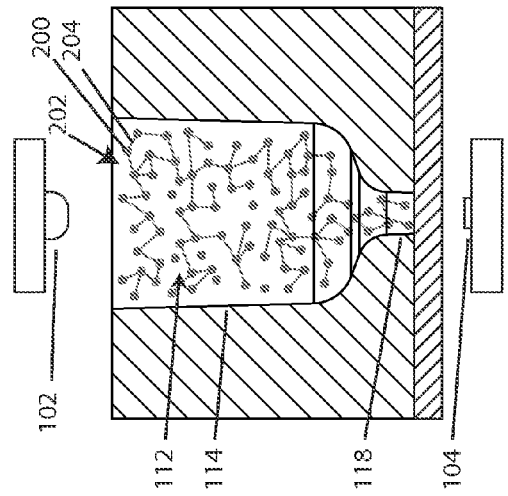
FIGS. 2A to 2C illustrate operation of an optical density agglutination detection system in accordance with the technology of the present application.
Figure 2B:
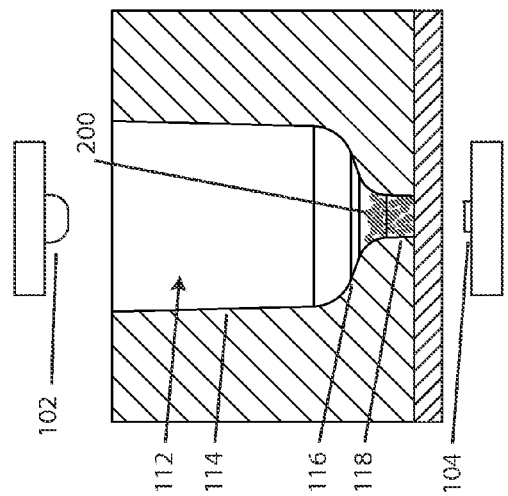
Figure 2A:
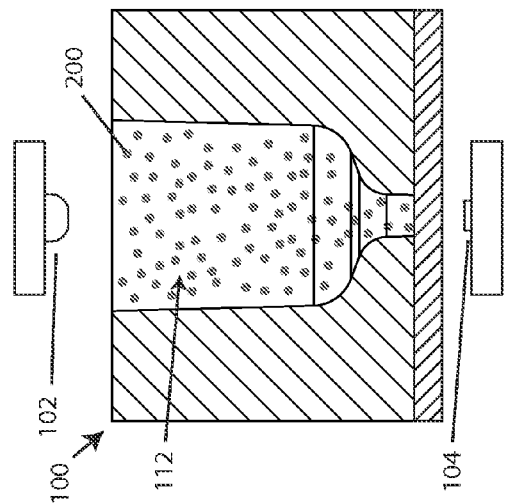

Operation—FIGS. 2A-2C

FIGS. 2A to 2C illustrate the operation of one embodiment of an optical density agglutination detection system 100. In FIG. 2A, light is emitted by light source 102 and transmitted through reaction vessel 112 containing components of an agglutination reaction. Light that is transmitted through reaction vessel 112 is detected by light detector 104. The output signal generated by light detector 104 varies with the intensity of light detected, and is read by an instrument, not specifically shown. Voltage readings, for example, from light detector 104 are interpreted by the instrument and used to return a result indicating agglutination or lack thereof in an agglutination reaction in reaction vessel 112.

FIG. 2A shows reaction vessel 112 containing components of an agglutination reaction that comprise particles 200 freely suspended in a reaction medium. Light source 102 emits light that passes through reaction vessel 112 having components of an agglutination reaction suspended therein. The intensity of light $I_1$ transmitted through a reaction medium can be expressed as an exponential function of optical density D, and incident intensity $I_0$ according to, $$I_1 = I_0 e^{-D}.$$

The Beer-Lambert Law further states that the optical density D of a light path of length L through a medium containing particles at concentration C having extinction coefficient x is given by, $$D = xLC.$$

For a light path of cross-sectional area A containing N particles, the optical density is then given by, $$D = \frac{xN}{A}.$$

Thus for a light path of fixed cross-sectional area A, the intensity of transmitted light $I_1$ is dependent upon the number of particles in the light path.

In one embodiment, the intensity of transmitted light through reaction vessel 112 depends upon the number of particles in the light path through reaction vessel 112. In one embodiment, the output voltage of light detector 104 is also dependent upon the number of particles in the light path through reaction vessel 112. The output voltage of the light detector 104 can be measured repeatedly by an automated sampler comprising a microprocessor, not specifically shown.

FIG. 2B illustrates the outcome of an agglutination reaction in reaction vessel 112 in which no agglutination has occurred. In the absence of agglutination, particles 200 settle under the influence of gravity (or other forces) and by virtue of the sloped reaction vessel transition region 116 are concentrated in the lower volume 118 of reaction vessel 112. Because well plate top 108 is substantially opaque, light is confined to a path with cross sectional area equal to cross-sectional area of lower volume 118. Because lower volume 118 has a smaller cross-sectional area than upper volume 114, some of particles 200 settling in reaction vessel 112 are caused to move from outside a light path between light source 102 and light detector 104 to inside the light path, thus increasing the optical density of the light path and decreasing the intensity of light detected by light detector 104. A decrease in intensity of light at light detector 104 causes a change in voltage output from light detector 104 that is interpreted as an absence of agglutination when the voltage output crosses a predetermined threshold.

In an absence of agglutination, particles that were initially distributed throughout upper volume 114 having radius $R_1$ settle into lower volume 118 having radius $R_2$. Thus in an embodiment and in the absence of agglutination, the average optical density of the light path from light source 102 to light detector 104 through the reaction medium is expected to increase by a factor approximately equal to the square of the ratio of $R_1$ to $R_2$. Thus, to increase the change in signal in the absence of agglutination, in one embodiment the ratio $R_1$ to $R_2$ is increased subject to the conditions that lower volume 118 is large enough to accommodate all of the particles in an agglutination reaction, and forms a small fraction of the overall volume of reaction vessel 112.

FIG. 2C illustrates the outcome of an agglutination reaction in reaction vessel 112 in which agglutination has occurred. During the process of agglutination, a rigid agglutination complex 202 is formed by cross-linkages 204 between a plurality of particles 200. The agglutination complex 202 inhibits particles from settling under the influence of gravity (or other forces), and from concentrating in lower volume 118 of reaction vessel 112. As can be appreciated, the size of the complex 202 inhibits its ability to settle in the smaller lower volume 118 In the case of agglutination, particles 200 and a portion of complex 202 remain distributed throughout reaction vessel 112, the optical density of the light path between light source 102 and light detector 104 remains substantially unchanged, and the intensity of light emitted by light source 102 and detected by light detector 104 remains substantially unchanged. Small or no changes in intensity of light at light detector 104 are expressed as small or no changes in voltage output from light detector 104 that signify the occurrence of agglutination as the aforementioned predetermined threshold is not crossed by the voltage output.

In accordance with an embodiment, agglutination detection system 100 may be connected to, or form part of, an instrument comprising various components including, but not limited to, an electrical control system, a microcontroller, a user interface, and one or more power supplies. The instrument may supply power to light source 102 and light detector 104, and may also measure and record voltages output by light detector 104. The instrument may also perform automated interpretation of output voltages from light detector 104 according to an algorithm in order to detect agglutination or the absence thereof, thus eliminating subjectivity and reducing variability in interpretation. The user interface may permit a user to control the instrument, and may be used by the instrument to report agglutination assay results to a user.

Other Embodiments

FIGS. 3-8

FIGS. 3-6 show similar agglutination detection systems in accordance with other embodiments.

Figure 3:
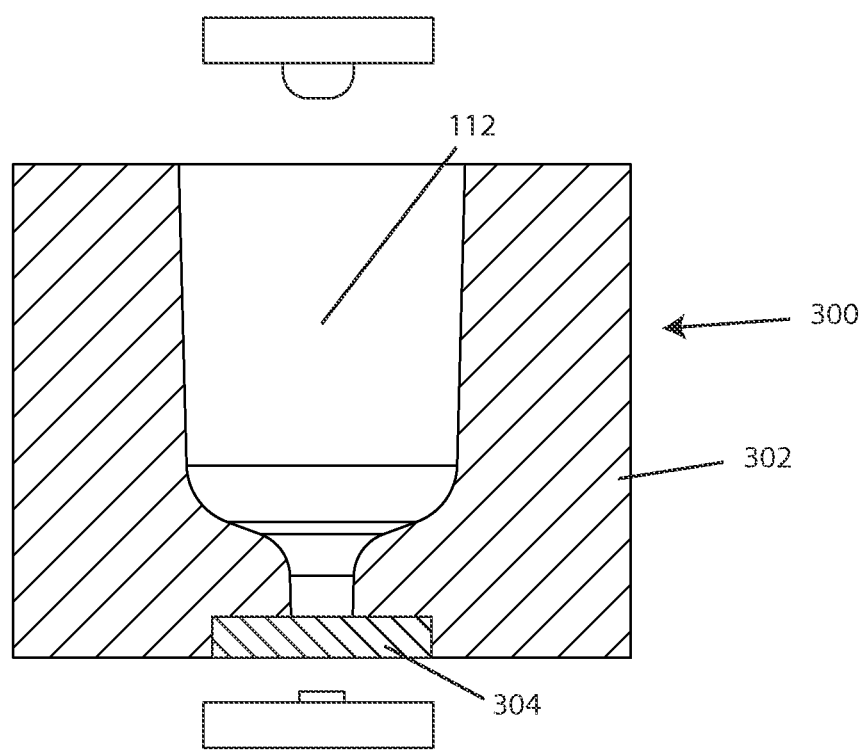
FIG. 3 shows an agglutination detection system in accordance with the technology of the present application.

In FIG. 3, well plate 300 is manufactured such that well plate bottom 304 is attached to well plate top 302 in a recess in the bottom of well plate top 302, according to another embodiment.

Figure 4:
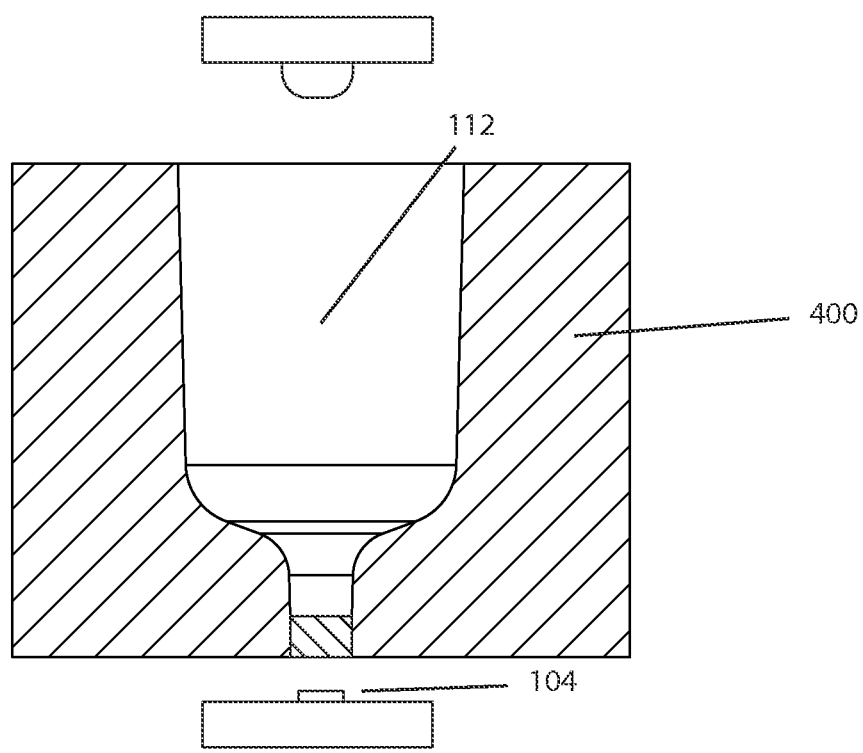
FIG. 4 shows an agglutination detection system in accordance with the technology of the present application.

In FIG. 4, well plate 400 is monolithically constructed and is chemically or physically processed locally such that the bottom wall of reaction vessel 112 is made to be transparent to the majority of light detectable by light detector 104 in accordance with another embodiment.

Figure 5:
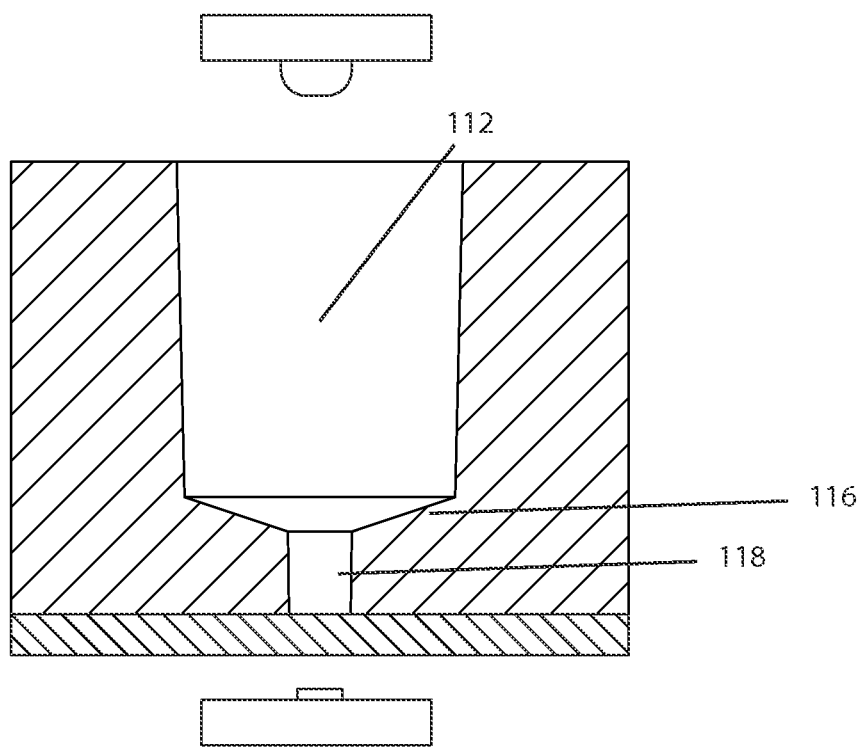
FIG. 5 shows an agglutination detection system in accordance with the technology of the present application.

In FIG. 5, the profile of reaction vessel transition region 116 takes an angular shape from large diameter to small diameter, with the provision that the reaction vessel transition region 116 slopes generally downwards and inwards towards the light path to concentrate settling particles in lower volume 118 in accordance with another embodiment.

Figure 6:
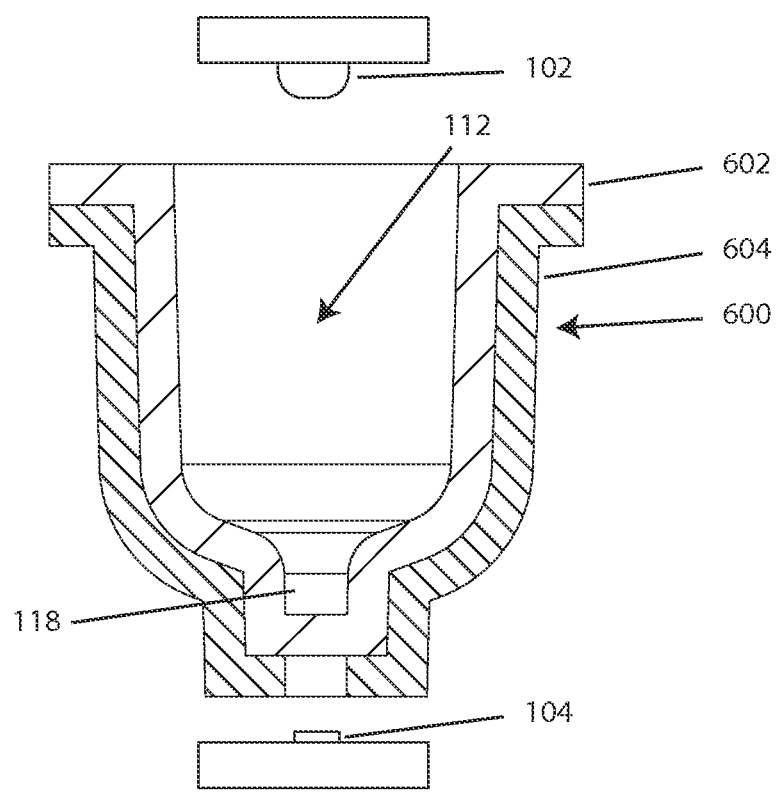
FIG. 6 shows an agglutination detection system in accordance with the technology of the present application.

In FIG. 6, well plate 600 comprises well plate top 602 and well plate shield 604. In this embodiment, well plate top 602 may be monolithically constructed and transparent. In an embodiment, well plate shield 604 is made to be opaque to the majority of light detectable by light detector 104, and substantially restricts light detected by light detector 104 to light which has passed through lower volume 118 of reaction vessel 112. In this embodiment, well plate top 602 and well plate shield 604 may be bonded together. In other embodiments, well plate top 602 has at least one significant degree of freedom of motion relative to well plate shield 604.

Figure 7A:
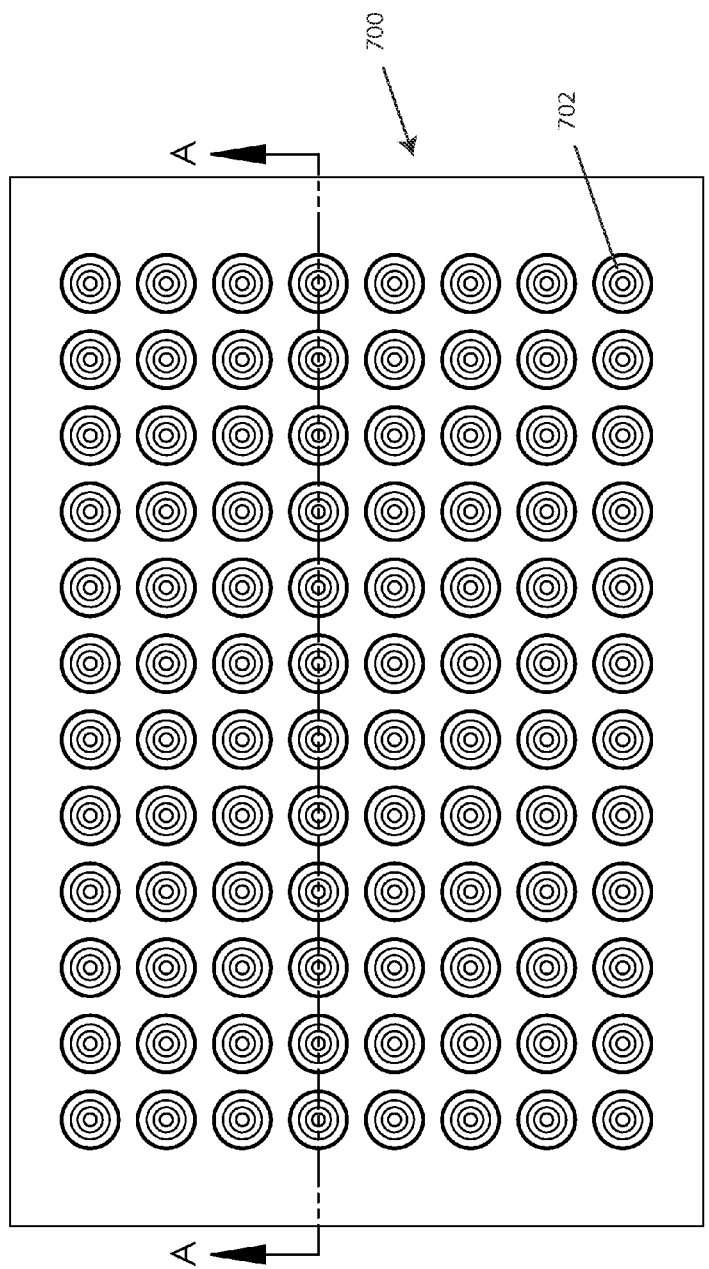
FIGS. 7A-7B show views of an arrayed well plate in accordance with the technology of the present application.
Figure 7B:
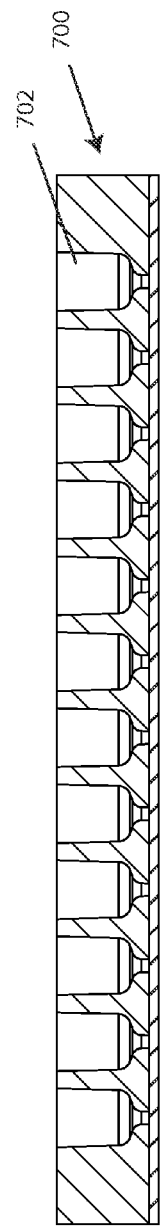

In FIGS. 7A and 7B, well plate 700 provides an array that comprises multiple reaction vessels 702, formed in accordance with any of the above embodiments or the like. FIG. 7A shows a top view, and FIG. 7B shows a section view taken through a vertical plane comprising line AA in FIG. 7A. While in FIGS. 7A and 7B each reaction vessel 702 is similar to a reaction vessel shown in FIG. 1, in other embodiments reaction vessels 702 may take other shapes or a variety of shapes within well plate 700, or may be manufactured in other ways in accordance with other embodiments.

During operation or use, one or more reaction vessels 702 of the array shown in well plate 700 may be reserved for performing measurements other than detection of agglutination in an agglutination assay. For example, a reaction vessel 702 may be left empty or filled with an unreactive liquid and the intensity of light emitted by a light source passing through such a reaction vessel may be measured to detect variations in the intensity of the emitted light over the course of a reaction.

FIGS. 8A to 8D illustrate various arrangements of light detectors 104 and light sources 102 that may be used with the arrayed well plate 700.

Figure 8A:
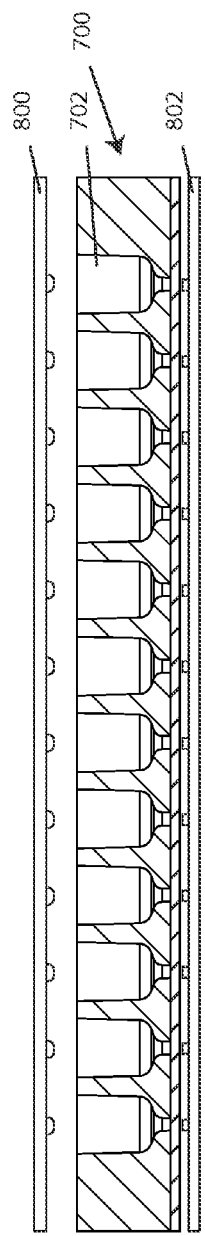
FIGS. 8A to 8D show arrangements of components of an arrayed optical density agglutination detection system in accordance with the technology of the present application.

FIG. 8A shows an arrayed light source 800 positioned above well plate 700, and an arrayed light detector 802 positioned below the well plate 700. For each reaction vessel 702, arrayed light source 800 comprises one or more light sources 102 and arrayed light detector 802 comprises one or more light detectors 104. Light detectors 104 are generally positioned so that light detectors 104 associated with a particular reaction vessel 702 substantially only detect light that has passed through that reaction vessel corresponding reaction vessel 702.

Figure 8B:
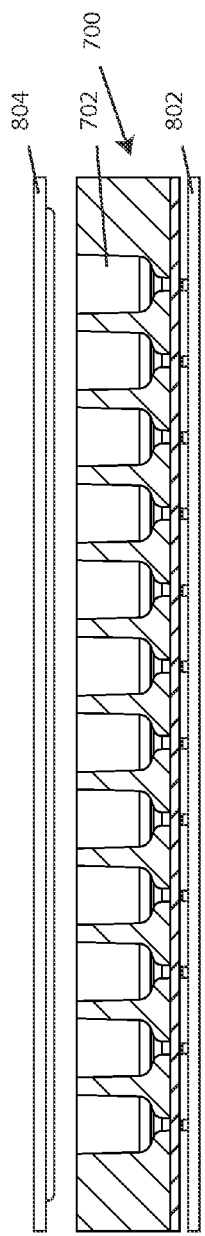
Figure 8C:
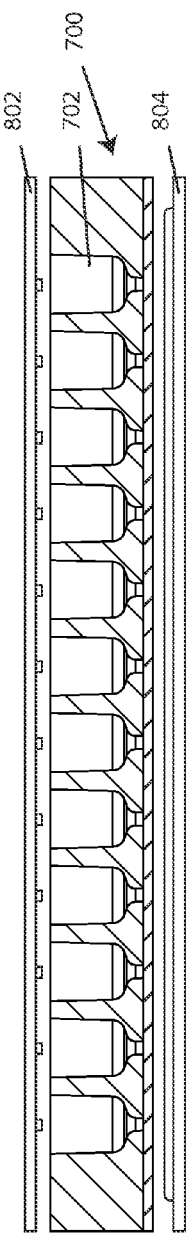
Figure 8D:
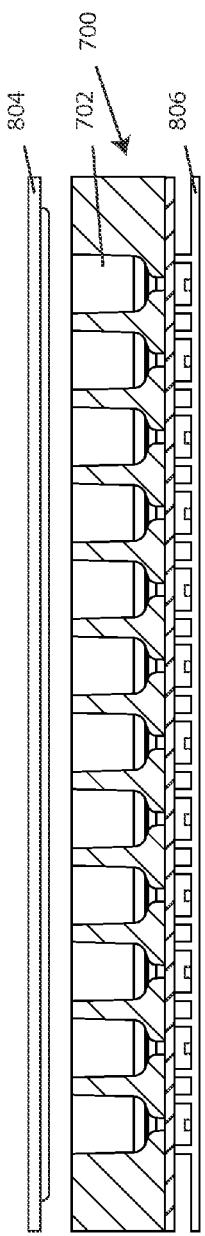

FIG. 8B shows a distributed light source 804 positioned above well plate 700. Distributed light source 804 serves as a light source for all reaction vessels 702 in arrayed well plate 700. FIG. 8C shows distributed light source 804 positioned below, and arrayed light detector 802 positioned above arrayed well plate 700. FIG. 8D shows isolated arrayed light detector 806 comprising opaque barriers between light detectors to prevent light detectors associated with a particular reaction vessel from detecting stray light passing through adjacent reaction vessels.

EXAMPLES

The following example is provided by way of illustration, not limitation.
Detection of Erythrocyte Agglutination by Influenza B Virus Using Optical Density A standard solution of turkey red blood cells (RBCs) in Alsever's solution (Lampire Biologicals, CAT NO. 7209403) was prepared before performing the agglutination assay. After gently mixing, 4 mL turkey RBCs was pipetted into a 15 mL conical tube. The solution was centrifuged at 2500 RPM for 10 minutes, and the Alsever's solution was removed. After adding 12 mL of phosphate-buffered saline (PBS) to the packed cells and mixing gently, the solution was centrifuged at 2500 RPM for 5 minutes. The supernatant was removed, and the same PBS wash step was repeated twice more. Once the final wash was complete, the volume of packed cells was estimated and an appropriate volume of PBS added to obtain a 10% RBC suspension. The 10% suspension was diluted 1:20 in PBS for use in the HA assay.

Three reactions were prepared and analyzed in an optical density agglutination detection system. Reaction A consisted of 50 μL of 0.5% turkey RBCs combined with 50 μL stock Influenza B control antigen (WHO reagent kit). Reaction B consisted of 50 μL of 0.5% turkey RBCs combined with 50 μL of PBS (negative control, no agglutinating reagent). Finally, Reaction C consisted of 100 μL of PBS, for use as a negative control and to measure variability in light source power output.

A single distributed laser light source (Laserglow Technologies series LBS-532-T) was used to illuminate all reaction vessels. The laser was allowed to warm up for 5 minutes before initiating the reactions. 100 μL of each of the reaction mixtures described above was pipetted into three separate reaction vessels in an arrayed well plate. Output signals from the arrayed light detector were collected over the course of 30 minutes using custom electronics and software, and the reaction vessels were evaluated for agglutination by eye at the end of the 30 minute time period.

Visual examination of each well yielded the expected results (data not shown): Reaction A exhibited agglutination of erythrocytes, no agglutination occurred in reaction B and erythrocytes settled to the lower volume of the reaction vessel, and no change was observed in the PBS in reaction C.

Figure 9:
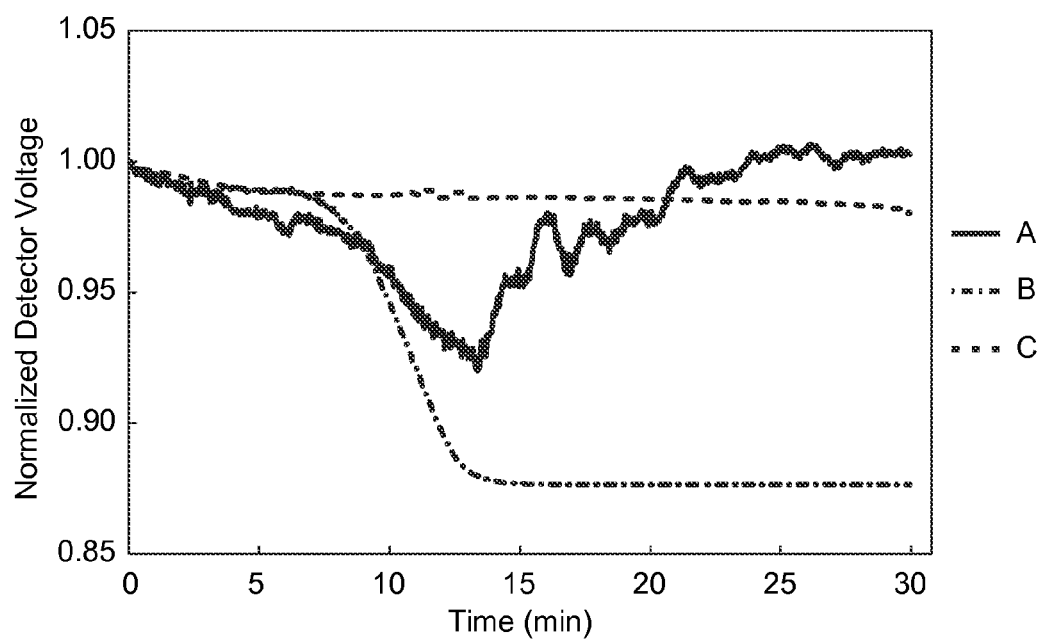
FIG. 9 shows a graph of output voltages versus time showing detection of agglutination by optical density measurement in accordance with the technology of the present application.

A striking signature of each reaction outcome was observed in the output voltage of the light detectors. FIG. 9 shows a graph of output voltage vs. time for each light detector as indicated; each trace is normalized to its initial value to facilitate comparison. In reaction A, in which agglutination occurred, no significant change in detector voltage was observed comparing starting and end point measurements. This behavior indicates no significant change in optical density through the reaction materials in the case of agglutination, as expected. In reaction B, detector output voltage exhibited a clear decrease as no agglutination occurred and erythrocytes settled to the lower volume of the reaction vessel. The decrease in transmitted light results from the increase in optical density of the light path through the reaction materials as erythrocytes are concentrated in the lower volume of the reaction vessel, as expected. Finally, in reaction C the output voltage varies very little over the course of the reaction. This control measurement indicates that any variations in output voltage caused by fluctuations in light intensity emitted by the light source can be neglected when compared to changes caused by cells settling in the lower volume of the reaction vessel.

Although the description above contains many specifics, these should not be construed as limiting the scope of the embodiments but as merely providing illustrations of some of several embodiments. For example, the arrayed well plate can have any number of reaction vessels; the distributed light source can be pixelated; the arrayed light detector may comprise more than one light detector associated with each reaction vessel in the arrayed well plate; the light source and light detector may be positioned so they do not lie on the axis of symmetry of the reaction vessel, etc.

Thus the scope of the embodiments should be determined by the appended claims and their legal equivalents, rather than by the examples given.

What is claimed is:
1. A method for detecting agglutination of particles comprising:
    providing one or more reaction vessels containing particles to be analyzed, each of the one or more reaction vessels comprising a light path and having a predetermined shape such that a force causes particles in each of the one or more reaction vessels to concentrate about the light path, such that the concentration increases an optical density of the light path,
    providing one or more light detectors positioned so as to be able to detect light travelling on the light path and capable of generating an electrical signal that varies with the intensity of the detected light, and
    providing a processor to analyze the electrical signal from at least one of the one or more light detectors and output a signal indicative of agglutination in at least one of the one or more reaction vessels when the output signal is compared to a threshold;
    wherein at least one of the one or more reaction vessels comprises an upper volume, a lower volume, and a transition region positioned between the upper volume and the lower volume, the upper volume having a cross-sectional area greater than a cross-sectional area of the lower volume, and the transition region having a profile that cause particles to move from the upper volume into the lower volume to be concentrated about the light path, and the profile of the transition region comprises two curved sections;

passing light along said light path through said reaction vessels to said one or more light detectors to generate said electrical signal that varies with the intensity of detected light; and detecting agglutination of particles based on said electrical signal.

2. The method of claim 1, further comprising one or more light sources capable of emitting light detectable by the one or more light detectors.

3. The method of claim 1, further comprising a display for reporting the results to a user.

4. The method of claim 1 wherein the one or more reaction vessels have an inside surface that is biocompatible and chemically compatible with components of an agglutination reaction.

5. The method of claim 1 wherein the one or more reaction vessels have a bottom wall that is transparent to light detectable by at least one of the one or more light detectors and the one or more reaction vessels have sides that are opaque to light detectable by at least one of the one or more light detectors.

6. The method of claim 1 further comprising a plurality of reaction vessels, wherein at least one of the one or more reaction vessels has a shape that is different than at least one other of the one or more reaction vessels.

7. A device for detecting agglutination of particles comprising:
one or more reaction vessels, each of the one or more reaction vessels comprising a light path and having predetermined shape such that a force causes particles in at least one of the one or more reaction vessels to concentrate about the light path so as to cause an increase in an optical density of the light path,
one or more light detectors positioned so as to be able to detect light travelling on the light path, wherein the one or more light detectors generates an electrical signal that varies with an intensity of the detected light, and
a processor to analyze the electrical signal from at least one of the one or more light detectors and output an indication of agglutination in at least one of the one or more reaction vessels by comparing the output to a threshold,
wherein at least one of the one or more reaction vessels comprises an upper volume, a lower volume, and a transition region positioned between the upper volume and the lower volume, the upper volume having a cross-sectional area greater than a cross-sectional area of the lower volume, and the transition region having a profile that cause particles to move from the upper volume into the lower volume to be concentrated about the light path, and
wherein the profile of the transition region comprises two curved sections.

8. The device of claim 7, further comprising one or more light sources capable of emitting light detectable by the one or more light detectors.

9. The device of claim 7, further comprising a display for displaying the results to a user.

10. The device of claim 7 wherein the one or more reaction vessels have an inside surface that is biocompatible and chemically compatible with components of an agglutination reaction.

11. The device of claim 7 wherein the one or more reaction vessels have a bottom wall that is transparent to light detectable by at least one of the one or more light detectors and the one or more reaction vessels have sides that are opaque to light detectable by at least one of the one or more light detectors.

12. The device of claim 7 further comprising a plurality of reaction vessels, wherein at least one of the one or more reaction vessels has a shape that is different than at least one other of the one or more reaction vessels.

* * * * *